United States Patent [19]

Stamler et al.

[11] Patent Number: 5,459,076
[45] Date of Patent: Oct. 17, 1995

[54] METHOD FOR DETECTING NITRIC OXIDE, NITROSONIUM EQUIVALENTS, S-NITROSOTHIOLS AND S-NITROSO-PROTEINS IN BIOLOGICAL SYSTEMS

[75] Inventors: Jonathan Stamler, Chapel Hill, N.C.; Joseph Loscalzo, Dedham, both of Mass.

[73] Assignee: Brigham and Women's Hospital, Boston, Mass.

[21] Appl. No.: 872,237

[22] Filed: Apr. 22, 1992

[51] Int. Cl.$^6$ ............... G01N 33/00; G01N 21/76
[52] U.S. Cl. ............... 436/116; 436/86; 436/106; 436/107; 436/114; 436/172
[58] Field of Search ............... 436/86, 63, 106, 436/107, 114, 116, 172, 175; 422/52

[56] References Cited

U.S. PATENT DOCUMENTS

| | | | |
|---|---|---|---|
| 3,967,933 | 7/1976 | Etess et al. | 422/52 X |
| 3,973,910 | 8/1976 | Fine | 436/107 |
| 4,066,411 | 1/1978 | Fine et al. | 422/70 X |
| 4,193,963 | 3/1980 | Bruening et al. | 436/116 X |
| 4,236,895 | 12/1980 | Stahl | 436/116 |
| 4,303,419 | 12/1981 | Frank et al. | 422/52 X |
| 4,335,073 | 6/1982 | Sherwood et al. | 422/52 X |
| 4,368,262 | 1/1983 | Bucovaz et al. | 435/13 X |
| 4,822,564 | 4/1989 | Howard | 422/52 |
| 4,843,016 | 6/1989 | Fine | 422/52 X |
| 5,002,964 | 3/1991 | Loscalzo | 514/423 |
| 5,025,001 | 6/1991 | Loscalzo et al. | 514/91 |
| 5,094,815 | 3/1992 | Conboy et al. | 422/52 |

FOREIGN PATENT DOCUMENTS 0210449  2/1987  European Pat. Off. .

OTHER PUBLICATIONS

Stamler et al. "S–Nitrosylation of Proteins . . ." Proceedings National Academy Sciences, vol. 89, pp. 444–448, Jan. 1992.

Pignatelli et al., "Group–Selective Determination of Total N–Nitroso Compounds In Nitrate–containing Human Urine Samples", *Analyst* 114:1103–1108 (1989).

Konstantinides et al., "Pyrochemiluminescence: Real–Time, Cost–Effective Method for Determining Total Urinary Nitrogen in Clinical Nitrogen–Balance Studies", *Clin. Chem.* 34(12):2518–2520 (1988).

Skogerboe et al., "Chemiluminescent Measurement of Total Urinary Nitrogen for Accurate Calculation of Nitrogen Balance", *Clin. Chem.* 36(5):752–755 (1990).

Kandil et al., "Letter to the Editor", *Clinica Chimica Acta* 208:135—136 (1992).

Gough et al., "An Examination of Human Blood For The Presence of Volatile Nitrosamines", *Fd. Chem. Toxic.* 21(2):151–156 (1983).

Eisenbrand et al., "II.4.b Determination of Volatile Nitrosamines in Food, . . . Chemilumescence Detection", *IARC Sci. Publ. Environ. Carcinog: Sel. Methods Anal.* 45:181–203 (1983).

Ward et al., "Nitrogen Estimation in Biological Samples By

(List continued on next page.)

*Primary Examiner*—James C. Housel
*Assistant Examiner*—Maureen M. Wallenhorst
*Attorney, Agent, or Firm*—Charles J. Herron; Elliot M. Olstein

[57] ABSTRACT

Nitric oxide, nitrosonium, S-nitrosothiols, and S-nitroso-proteins can be detected in biological samples, using a method which involves injection of samples into a photolysis cell, prior to detection of chemiluminescence generated by the reaction between nitric oxide and ozone. To detect S-nitrosothiols and S-nitroso-proteins separate aliquots of the same samples are subjected to pretreatment with mercurous ion, and a protein-precipitating agent, respectively, and the resulting nitric oxide signals are compared to those generated by untreated samples. This method is useful for monitoring the levels of nitric oxide bioactivity in both normal physiological states, and disease states, such as septic shock, atherosclerosis, thrombosis, hyperhomocysteinemia, pulmonary hypertension, malignancy, infections and central nervous systems disorders.

7 Claims, 3 Drawing Sheets

OTHER PUBLICATIONS

Use of Chemiluminescence", *Clin. Chem.* 26(9):1336–1339 (1980).

Webster's Deluxe Unabridged Dictionary, Second Edition, p. 5.

Bassenge, "Clinical Relevance of Endothelium–Derived Relaxing Factor", *Br. J. Clin. Pharmac.* 34:37S–42S (1992).

Creager et al., "L–Arginine Improves Endothelium–Dependent Vasodilation in Hypercholesterolemic Humans", *J. Clin. Invest.* 90:1248–1253 (1992).

Haefliger et al., "Nitric Oxide And Endothelin–1 Are Important Regulators of Human Ophthalmic Artery", *Invest. Ophthalmol. Vis. Sci.* 33(7):2340–2343 (1992).

Änggård, E. E., "Endogenous and Exogenous Nitrates", *Acta Anaesthesiol. Scand.* 36(Suppl 97):7–10 (1992).

Kilbourn et al., "Reversal of Endotin–Mediated Shock by Ng–Methyl–L–Arginine, An Inhibitor Of Nitric Oxide Synthesis", *Biochem. Biophys. Res. Comm.* 172(3):1132–1138 (1990).

Stamler et al., "Nitric Oxide Circulates in Mammalian Plasma Primarily As An S–Nitroso Adduct of Serum Albumin", *Proc. Natl. Acad. Sci. USA* 89:7674–7677 (1992).

Archer et al., *IARC Sci. Publ.* 31:305–318 (1980).

Arroyo et al., *Free Rad. Res. Comms.* 14(2):145–155 (1991).

Downes et al., *Analyst* 101:742–748 (1976).

Feltes et al., *Journal of Chromatography* 518:21–40 (1990).

Furchgott et al., *Nature* 288:373–376 (1980).

Goretski et al., *Journal of Biol. Chem.* 263(5):2316–2323 (1988).

Kelm et al., *Circulation Research* 66(6):1561–1575 (1990).

Kowaluk et al., *J. Pharmacology and Experimental Therapeutics* 255(3):1256–1264 (1990).

Martin et al., *J. Pharmacology and Experimental Therapeutics* 237(2):529–538 (1986).

Moncada et al., *Biochemical Pharmacology* 38(11):1709–1715 (1989).

Morris et al., *Applied and Environmental Microbiology* 42(6):958–962 (1981).

Oae et al., *Organic Preparations and Procedures Int.* 15(3):165–198 (1983).

Oka et al., *Journal of Chemical Physics* 66(2):713–721 (1977).

Palmer et al., *Nature* 327:524–526 (1987).

Pragst, F., *J. Electroanal. Chem.* 119:315–330 (1981).

Saville, B., *Analyst* 83:670–672 (1958).

Westenberger et al., *Free Rad. Res. Comms.* 11:167–178 (1990).

METHOD FOR DETECTING NITRIC OXIDE, NITROSONIUM EQUIVALENTS, S-NITROSOTHIOLS AND S-NITROSO-PROTEINS IN BIOLOGICAL SYSTEMS

This invention was made with government support under HL40411, HL343344, K08HL02582, K04HL02273, awarded by the National Institutes of Health, a Merit Award from the Veteran's Administration, and Office of U.S. Naval Blood Research Contract N00014-88-C-0118. The government has certain rights in the invention.

BACKGROUND OF THE INVENTION

1. Field Of The Invention

The invention relates to a method for detecting nitric oxide and nitrosonium equivalents in a biological sample, involving subjecting a biological fluid to photolysis prior to chemiluminescence detection by reaction with ozone. The invention further relates to a method for detecting S-nitrosothiols and S-nitroso-proteins in a biological sample, which involves treating the samples with mercury and a protein-precipitating agent, respectively, prior to chemiluminescence detection, and comparing with the chemiluminescence signal generated by a sample absent said treatment.

2. Brief Description Of The Background Art

Endothelium-derived relaxing factor (EDRF), is a product of the normal endothelial cell, and has both vasodilatory and antiplatelet properties (Furchgott, R. F. et al., *Nature* 288:373–376 (1980); Moncada, S. et al., *Biochem. Pharmacol.* 38:1709–1713 (1989); Azuma, H. et al., *Brit. J. Pharmacol.* 88:411–415 (1986) and Radomski, M. W. et al., *Brit. J. Pharmacol.* 92:639–642 (1987)). Pharmacologic studies suggest that disease states as varied as septic shock, hyperhomocysteinemia, atherosclerosis, and hypoxia-induced pulmonary hypertension may be associated with abnormal concentrations of EDRF in the vascular milieu (Westenberger, U. et al., *Free Rad. Res. Comm.* 11:167–168 (1990); Yamamoto, H. et al., *J. Clin. Invest.* 81:1752–1758 (1988); Dinh-Xuan, A. T. et al., *Engl. J. Med.* 324:1539–1547 (1991)). This bioactive substance is believed to be equivalent to nitric oxide, or a chemical congener or adduct thereof (Palmer, R. M. G. et al., *Nature* 327:524–525 (1987); Ignarro, L. J. et al., *Proc. Natl. Acad. Sci.* 84:9265–9269 (1987)). Among the species of importance as biological adducts of nitric oxide are S-nitrosothiols-, which are adducts with the sulfhydryl groups of amino acids, peptides, and proteins.

It has been demonstrated that nitric oxide and authentic EDRF react with free thiol groups of proteins under physiologic conditions in vitro, to form S-nitroso-proteins. These nitric oxide adducts have bioactivities which are comparable to nitric oxide, but exhibit half-lives on the order of hours, significantly longer than that of EDRF (Stamler, J. S. et al., *Proc. Natl. Acad. Sci.* 89:444–448 (1992)). The single free cysteine present on serum albumin (cysteine 32) is particularly reactive toward nitrogen oxides (most likely nitrosonium ion) under physiologic conditions, primarily because of its anomalously low pK, and its abundance in plasma, where it accounts for an approximate 0.5 mM thiol concentration.

Under normal circumstances, the concentration of nitric oxide in blood or plasma is believed to be quite low (in the 1 nM range) and its half life of the order of 0.1 second. Its high degree of reactivity toward oxygen and redox metals, in conjunction with its extremely short half-life, have made the routine measurement of blood levels in both normal and disease states most difficult by standard methods, such as chemiluminescence spectroscopy, electron paramagnetic resonance spectroscopy, or differential absorbance spectroscopy of hemoglobin (Martin, W. et al., *J. Pharmacol. Exp. Therap.* 237:529–538 (1986); Downes, M. J. et al., *Analyst* 101:742–748 (1976); Kelm, M. et al., *Circ. Res.* 66:1561–1575 (1990); Arroyo, C. M. et al., *Free Rad. Res. Comm.* 14:145–155 (1991) and Goretsky J. et al., *J. Biol. Chem.* 263:2316–2323 (1988)). In fact, it is generally assumed in the field that such measurements are not feasible by currently used methods.

Nitrosonium ($NO^+$) is a short lived species which is too unstable to exist freely in biological systems, and felt to be non-detectable by chemiluminescence. Nitric oxide exists in the S-nitrosothiol adduct, not as nitric oxide but rather as a nitrosonium equivalent. Thus, it behaves chemically in a manner which more closely resembles $NO^+$, than NO• (nitric oxide). S-nitrosothiols have not been detected by chemiluminescence and it is generally not appreciated in the art that nitrosonium is a biologically relevant species.

Chemiluminescence spectroscopy has been used, in particular, to detect nitric oxide in studies of EDRF in vitro. By the standard analysis, however, samples to be tested are subjected to extensive chemical pretreatment that precludes the discrimination of free nitric oxide, from nitrosonium, labile adducts or from higher oxidation states of nitrogen. Given the demonstration by these investigators of the importance of nitric oxide adducts (nitrosonium adducts), such as S-nitrosothiols and S-nitroso-proteins, in biological systems, a need exists for an analytical method which enables one to distinguish these compounds from nitric oxide, and thereby detect and quantify them in biological samples.

SUMMARY OF THE INVENTION

The invention relates to a method for detecting nitric oxide and nitrosonium in a biological fluid sample comprising the steps:

a. subjecting said sample to photolysis;

b. quantitating the amount of nitric oxide in said sample by the signal generated by a chemilumenscence reaction.

The invention further relates to a method for detecting low-molecular weight S-nitrosothiols in a biological fluid, comprising the further steps:

a. detecting total nitric oxide in a biological fluid in accordance with the method of claim 1:

b. inactivating the chemiluminescence signal-generating capability of any nitric oxide which is associated with a thiol, in a separate sample of the equivalent biological fluid;

c. detecting the nitric oxide in the sample obtained by step (b) in accordance with the method of claim 1; and d. determining the quantitative difference between steps (a) and (c) to determine the amount of thiol-bound nitric oxide.

The invention further relates to a method for detecting S-nitroso-proteins in a biological fluid sample, comprising further steps:

a. detecting total nitric oxide in accordance with the method of claim 1;

b. removing the chemiluminescence signal-generating capability of any nitric oxide which is associated with a protein, in a separate sample of the equivalent biological fluid;

c. detecting the nitric oxide in the sample obtained by step (b); and d. determining the quantitative difference between steps (a) and (c) to determine the amount of protein-bound nitric oxide.

The invention further relates to a method for determining the presence of a disease state involving abnormal levels of nitric oxide and nitrosonium equivalents, using the methods of the invention to detect S-nitrosothiols and S-nitroso-proteins in the biological fluids of a patient.

The invention further relates to a method for monitoring the extent of a disease state involving abnormal levels of nitric oxide and nitrosonium equivalents, using the methods of the invention to detect S-nitrosothiols and S-nitroso-proteins in the biological fluids of a patient. In particular, said disease state may be selected from the group comprised of septic shock, cardiogenic shock, hypovolemic shock, atherosclerosis, hyperhomocysteinemia, venus thrombosis, arterial thrombosis, coronary occlusion, pulmonary embolism, cerebrovascular accidents, vascular fibrosis, ectopia lentis, osteoporosis, mental retardation, skeletal deformities, pulmonary hypertension, malignancy, infection and central nervous system disorders.

The invention also relates to the methods of the invention wherein the biological fluid sample is selected from the group comprising blood, serum, cerebrospinal fluid, semen, synovial fluid, peritoneal fluid, intestinal secretions, sputum, stool, saliva, corneal fluid, amniotic fluid and perspiration.

DESCRIPTION OF THE PREFERRED EMBODIMENTS

S-nitrosothiols and S-nitroso-proteins serve as a reservoir for nitric oxide produced by vascular endothelial cells and white blood cells. Consequently, the inventors discovered a photolytic-chemiluminescence method for detection of free nitric oxide, nitrosonium equivalents, S-nitrosothiols, and S-nitroso-proteins in biologic systems.

In one embodiment, the invention relates to a method for detecting nitric oxide in a biological fluid, comprising subjecting the sample to photolysis prior to chemiluminescence detection with ozone. Analytical parameters and conditions are determined by routine methods available to those in the art. Examples of biological fluids include blood, serum, urine, cerebrospinal fluid, semen, synovial fluid, peritoneal fluid, intestinal secretions, sputum, stool, saliva, corneal fluid, amniotic fluid and perspiration.

Another embodiment of the invention relates to a method for detecting nitric oxide equivalents in a biological fluid, which utilizes a chemiluminescence apparatus in which a photolysis cell is linked directly to the reaction chamber and detector portion, thereby bypassing the pyrolyzer. A sample of the biological fluid is injected into the photolysis cell, either directly, or as chromatographic effluent from a high-performance liquid or gas chromatography system, which is connected to the photolysis cell. Prior to subjecting the sample to photolysis, the sample may be centrifuged to remove hemoglobin and other blood components.

The sample is then irradiated with a mercury vapor lamp, and directed through a series of cold traps, where liquid and gaseous fractions which are less volatile than nitric oxide (such as nitrite and nitrate) are eliminated, leaving only free nitric oxide remaining in the cell. The nitric oxide is then transported by a gaseous stream, preferably helium, into the chemiluminescence spectrometer. In the alternative, other inert gases may be used.

Once present in the chemiluminescence spectrometer, the free nitric oxide is detected by its chemical reaction with ozone, resulting in the generation of signals that are recorded on a digital integrator. In a preferred mode, flow rates and illumination levels in the photolysis cell are designed to cause complete photolysis of the S-nitric oxide bond of the S-nitrosothiol compounds. However, flow rates and illumination levels may be adjusted by routine methods available in the art, in order to achieve optimal cleavage of the bond between the particular adduct and nitric oxide, nitrosonium or nitroxyl whichever is bound.

In another embodiment, the invention relates to a method for detecting S-nitrosothiols in a biological fluid comprising inactivating the chemiluminescence, signal-generating capability of any nitric oxide which is associated with a thiol, in said sample, and determining the amount of thiol-bound nitric oxide by measuring the quantitative difference between total nitric oxide and nitric oxide remaining after inactivation.

A particular embodiment of this method relates to a method in which the biological fluid is treated with a mercurous ion, followed by air incubation, which oxidizes the nitric oxide and nitrosonium and renders them undetectable. Compounds suitable for pretreatment include $Hg_2Cl_2$, and other mercurous ion salts and organic mercurials. The treated sample is then injected into the photolysis cell, and the nitric oxide is detected by the chemiluminescence method described above. The amount of nitric oxide which is specifically derived from S-nitrosothiols is determined by comparing the chemiluminescence signal generated by the mercurous ion-treated sample, with a chemiluminescence signal generated by a sample of the equivalent biological fluid which is not treated with mercurous ion prior to injection into the photolysis cell.

An additional embodiment of the claimed invention relates to a method for detecting S-nitroso-proteins in biological fluids. In this method, the biological fluid is treated with a protein-precipitating agent, which effectively removes protein-bound nitric oxide and nitrosonium. Suitable protein-precipitating compounds include trichloroacetic acid, acetone, phenol and ammonium sulfate. The treated sample is then injected into the photolysis cell and the nitric oxide is detected by the chemiluminescence method described above. The amount of nitric oxide derived from S-nitroso-proteins is determined by comparing the chemiluminescence signal generated by the treated sample, with a chemiluminescence signal generated by a sample of equivalent biological fluid which is not treated with a protein-precipitating agent prior to injection into the photolysis cell.

In a further embodiment of the claimed invention, the methods described above may be utilized to determine the presence of a disease state which involves abnormal levels of nitric oxide and its biologically active equivalents, by monitoring S-nitrosothiol and S-nitroso-protein levels in the biological fluids of a patient. As the inventors have demonstrated, these nitric oxide adducts represent a pool of bioactive nitric oxide in physiological systems. Therefore, in disease states in which the pathogenesis derives from the effects of abnormal levels of nitric oxide, these methods provide a means for the clinician to determine the presence of, and monitor the extent of, the disease state. Such information enables the clinician to determine the appropriate pharmacological intervention necessary to treat the disease state. Such disease states include, but are not limited to, septic shock, cardiogenic shock, hypovolemic shock, atherosclerosis, hyperhomocysteinemia, venous thrombosis, arterial thrombosis, coronary occlusion, pulmonary embolism, cerebrovascular accidents, vascular fibrosis, ectopia lentis, osteoporosis, mental retardation, skeletal deformities, pulmonary hypertension, malignancy, infections, and central nervous system disorders. Furthermore, the use of these methods is not limited to these diseases. It is predicted that this method will be of use in assaying biologically active nitric oxide equivalents in any organ in which nitric oxide is implicated.

The invention provides an analytical method that enables the determination of plasma levels of free nitric oxide, nitrosonium equivalents, S-nitroso-proteins and S-nitrosothiols. The use of photolysis converts $NO^+$ to $NO\bullet$ (nitric oxide), and provides evidence for the existence of $NO^+$ (in the form of nitrosothiols) in biological systems. Thus, this method is a novel means of detecting $NO^+$ equivalents and S-nitrosothiols, and by virtue of its remarkable sensitivity also detects nitric oxide, permitting its distinction from nitric oxide equivalents. Alternative methods for nitrosonium detection do not provide the requisite sensitivity for detection in biological assays.

Results derived from application of this method show that the concentration of S-nitrosothiols is three-to-four orders of magnitude greater than that of free nitric oxide in mammalian plasma. In addition, the S-nitrosothiol fraction is largely comprised of the S-nitrosothiol adduct of serum albumin. Further experiments demonstrate that the levels of S-nitroso-serum albumin change with inhibition of nitric oxide production in concert with changes in blood pressure. This methodology represents a simple technique for the sensitive, specific, and reproducible measurement of nitric oxide, nitrosonium equivalents and their thiol adducts, in biologic specimens, and has broad application in the analysis of nitric oxide levels in both normal and disease states.

Having now generally described the invention, the same will be more readily understood through reference to the following examples which are provided by way of illustration, and are not intended to be limiting of the present invention.

The entire text of all publications cited above and below are hereby incorporated by reference.

EXAMPLES

EXAMPLE 1: Detection of Nitric Oxide, S-nitrosothiols and S-Nitroso-proteins in Plasma

METHODS AND RESULTS

Initially, to modify the chemiluminescence apparatus for use in the detection method, a photolysis cell, consisting of a borosilicate glass coil (3 m×0.64 cm o.d.×1 mm i.d., turned to a diameter of 6 cm and a width of 12 cm), with a purge stream of helium (5 L/min), was linked directly to the reaction chamber and detector portion of a chemiluminescence apparatus (Model 543 Thermal Energy Analyzer, Termedix, Inc., Woburn, Mass.), thereby bypassing the pyrolyzer. Then, a 5–100 μl volume sample was either introduced directly, or as a chromatographic effluent from an attached high-performance liquid or gas chromatography system into the photolysis cell, and irradiated with a 200-watt mercury vapor lamp (vertically mounted in the center of the photolysis coil on TEFLON towers). The effluent from the photolysis coil was directed to a series of cold traps where liquid and gaseous fractions less volatile than nitric oxide (such as nitrite and nitrate), were removed.

The nitric oxide was then transported by a helium stream into the chemiluminescence spectrometer, in which free nitric oxide was detected by reaction with ozone. Signals were recorded on a digital integrator (Model 3393A, Hewlett Packard, Andover, Mass., USA). Flow rates and illumination levels in the photolysis cell were designed to result in complete photolysis of the S-nitric oxide bond, as confirmed by analysis of effluent from the photolysis cell, according to standard methods (Saville, B., *Analyst* 83:670–672 (1958)).

To determine the fraction of nitric oxide which was derived from S-nitrosothiols, several additional steps were included in the method described above. Prior to its injection into the photolysis cell, an aliquot of the same sample was treated with 8.9 mM $HgCl_2$ followed by air incubation, according to standard methods (Saville, B., *Analyst* 83:670–672 (1958)), in order to oxidize the nitric oxide displaced as nitrosonium, and render it undetectable. Nitric oxide concentrations from samples alternatively subjected to or not subjected to, pretreatment with $HgCl_2$, were compared, to determine how much of the nitric oxide detected was derived specifically from S-nitrosothiols. Similarly, as an added measure of confirmation, S-nitrosothiols and free nitric oxide were compared using nitric oxide concentrations in samples alternatively exposed to, or not exposed to, photolyzing illumination.

S-nitroso-proteins were detected by quantifying the amount of total nitric oxide signal that was removable by protein precipitation achieved with trichloroacetic acid. To eliminate the possibility that S-nitroso-proteins formed as a consequence of exposing a sample containing $NO_2$, to protein thiols as a result of the decrease in pH during acid precipitation, other agents such as acetone, phenol, and ammonium sulfate, were also used to precipitate protein without inducing a pH change. In all cases, the results were similar to those obtained with acid precipitation.

S-nitroso-L-cysteine, S-nitroso-glutathione, S-nitroso-N-acetyl-L-cysteine and S-nitroso-bovine serum albumin were synthesized by exposing the respective thiols to acidified $NaNO_2$, according to routine methods, and standard curves were generated (Stamler, J. S. et al. *Proc. Natl. Acad. Sci.* 89:444–448 (1992)). Similarly, standard curves were derived for nitric oxide generated from acidified $NaNO_2$, or from a saturated solution of nitric oxide gas serially diluted immediately before measurement in airtight syringes. Concentration-response curves were linear with correlation coefficients of ≥0.98 in all cases. Limits of sensitivity were approximately 0.1 pM, and intraassay variability was ±3%.

Blood samples, anticoagulated with 0.13M trisodium citrate, were obtained for analysis of plasma from normal volunteers; and from rabbits before, and 15, 30, 60, and 180 minutes following intravenous administration of a nitric oxide synthetase inhibitor, $N^G$-monomethyl-L-arginine (L-NMMA) (50 mg/kg, intravenous bolus). Each of these plasma specimens was injected directly into the photolysis cell, without the use of HPLC. In addition, each sample was compared with a corresponding control that included: (1) measurement without photolyzing illumination; (2) a determination after protein precipitation; and (3) a determination after addition of 8.9 mM $Hg_2Cl_2$ to the sample.

The response of this system to pure S-nitrosothiols was first examined using S-nitroso-L-cysteine as a standard. The concentration of the stock solution from which serial dilutions were made was determined by standard methods and confirmed by the optical density at 340 nm (Saville, B. Analyst 83:670–672 (1958); and Stamler, J. S. et al. Proc. Natl. Acad. Sci. 89:444–448 (1992)). Serial dilutions were prepared with concentrations ranging from 100 µM to 0.1 pM. The chemiluminescence signal was linear over this concentration range (correlation coefficient of ≥0.98).

As additional controls, S-nitroso-glutathione, and S-nitroso-N-acetyl-L-cysteine were also synthesized and responses measured. In the absence of photolysis, the nitric oxide signal was below the limits of detectability. Similarly, $HgCl_2$ pretreatment of the samples, followed by incubation in air to oxidize (and render undetectable) the liberated nitric oxide led to a loss of >99% of the chemiluminescence signal in all cases.

The fasting plasma of five normal volunteers (age 30±3 years) was next obtained for measurement of nitric oxide by this protocol. Blood samples were obtained in an evacuated sample tube containing 13 mM trisodium citrate, centrifuged at 700 g for 10 minutes, and the supernatant plasma removed in an air-tight syringe for transfer to the detection system. As shown in Table I, mean plasma levels (Table I) were 7.19± 5.73 µM, only 10.01% of which was not displaceable by $Hg^{2+}$, and 0.047% of which was detectable without photolysis. Furthermore, protein precipitation (with 5% trichloroacetic acid or 50% acetone) led to a loss of 96.25% of the signal.

S-nitroso-albumin forms under physiologic conditions, is very stable, and represents a carrier molecule in plasma for nitric oxide (Stamler, J. S. et al. Proc. Natl. Acad. Sci. 89:444–448 (1992)). Therefore, experiments were conducted to determine the fraction of nitric oxide bound to and carried in human plasma by serum albumin. Plasma specimens (three) were subjected to affinity chromatography using an Econo-Pac Blue five-ml column cartridge (BioRad, Richmond, Calif.) to which both the serum albumin and S-nitroso-serum albumin bound. The results showed that 82% of the total (protein) precipitable nitric oxide signal was eliminated by this procedure.

L-NMMA is a specific competitive inhibitor of the nitric oxide synthetases, the family of enzymes responsible for the elaboration of nitric oxide from L-arginine. Infusion of L-NMMA has been shown to induce an increase in blood pressure in rabbits and dogs implying a role for steady-state levels of EDRF in maintenance of blood pressure (Rees, D. D., et al. Proc. Natl. Acad. Sci. 86:3375–3378 (1989); and Chu, A. et al. Am. J. Physiol. 258:H1250–1254 (1990)).

Nitric oxide has a significant role in the regulation of vascular tone, and hence, the regulation of blood pressure. Thus, experiments were conducted to identify the relationship between blood pressure and depletion of plasma S-nitrosothiols, L-NMMA 50 mg/kg was infused as an intravenous bolus into three 3–4 kg female New Zealand white rabbits. As shown in Table II, within 15 minutes, the mean blood pressure (measured by a cannula placed in the femoral artery) increased 16% (from 64±5 to 74±6 nun Hg, p<0.05), and by one hour, the mean pressure increased by 22% (to 78±11, p<0.05).

Figure 1:
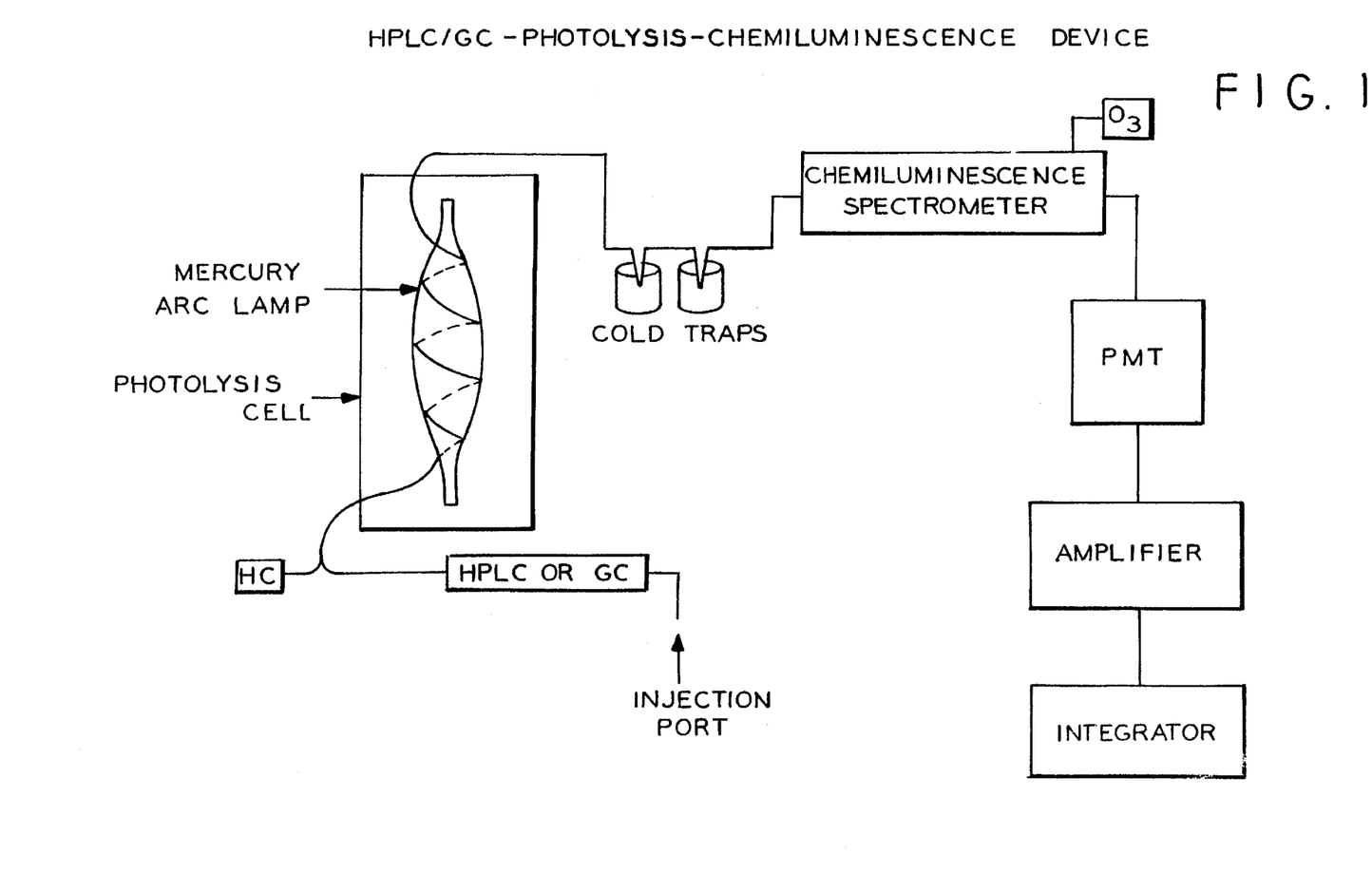
FIG. 1. Schematic representation of the GC/HPLC-photolysis-chemiluminescence system used to measure S-nitrosothiols in biologic samples. HC=helium canister, HPLC= high-performance liquid chromatography system, GC=gas chromatography system, PMT=photomultiplier tube.
Figure 2:
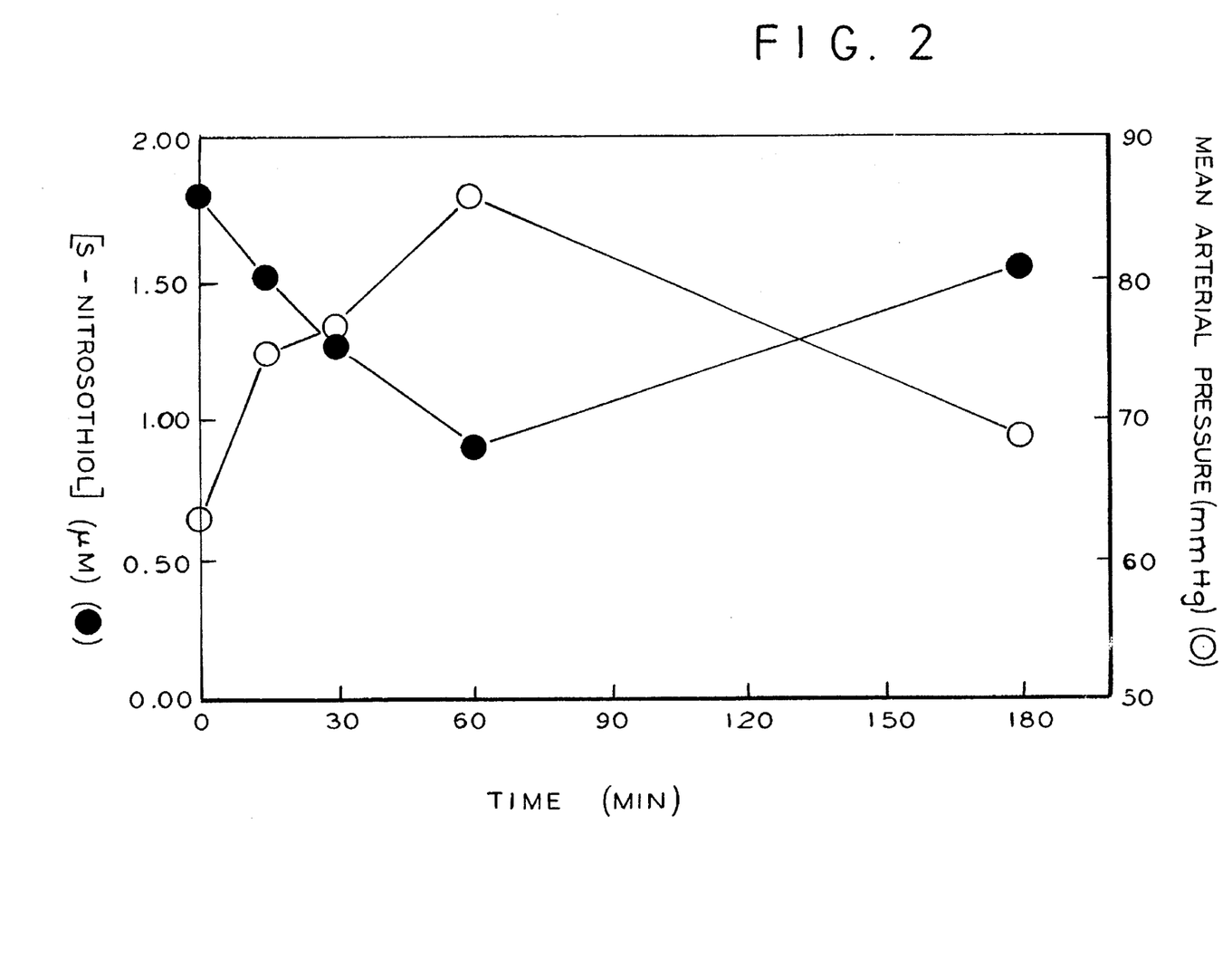
FIG. 2. Representative response in mean arterial pressure (open circles) and plasma S-nitrosothiols (closed circles) in a rabbit intravenously administered 50 mg/kg L-NMMA as a bolus infusion at t=0; by 180 minutes after administration of L-NMMA.

Concomitant with this increase in blood pressure, total S-nitrosothiols in plasma decreased by 14% at 15 minutes after infusion (1.29±0.57 µM to 1.11±0.51 µM), and by 40% at one hour (to 0.78± 0.26 µM, p<0.02). These changes occurred primarily in the S-nitroso-protein fraction of plasma, wherein 94.6% of total S-nitrosothiols was found before infusion of L-NMMA, and 92.9% by one hour after infusion. The time course of a typical experiment is shown in FIG. 2, where changes in mean blood pressure and total S-nitrosothiols are plotted in graphic form.

Initially after administration of L-NMMA, the mean arterial pressure increased with a time course similar to that for the complementary decrease in plasma S-nitrosothiols. Peak effects (maximum and minimum, respectively) were noted by 60 minutes, and by 180 minutes, both parameters returned to pretreatment values. Importantly, cross-over points are noted at 30 and 120 (interpolated) minutes, suggesting a mechanistic association between these two parameters. Again of note is the observation that only 0.26% of the total chemiluminescence signal could be accounted for by free nitric oxide (data not shown).

Figure 3:
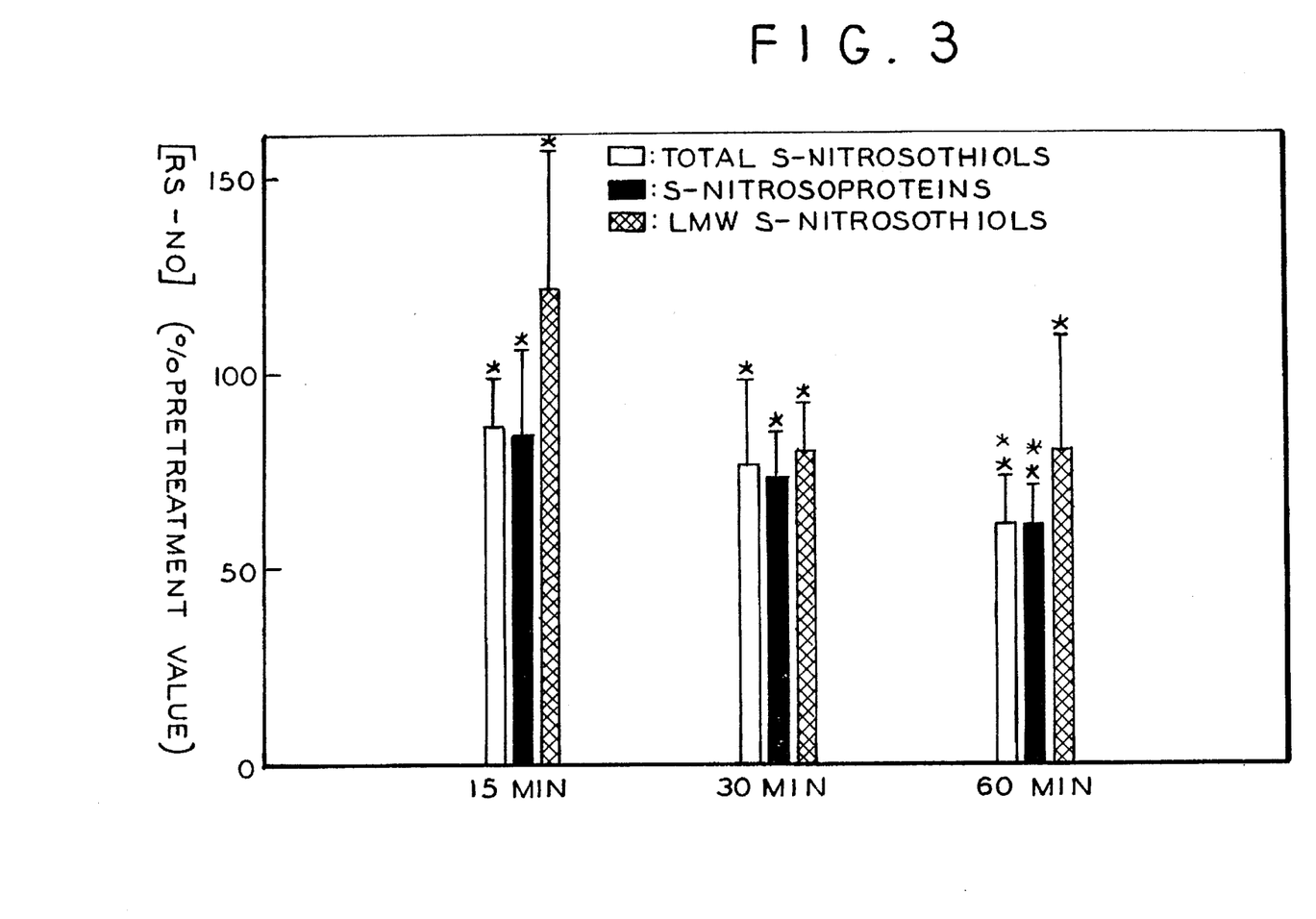
FIG. 3. Percentage changes in S-nitrosothiols in rabbit plasma following administration of 50 mg/kg L-NMMA at t=0. Total S-nitrosothiols (clear bars), S-nitroso-proteins (filled bars), and low-molecular-weight (LMW) S-nitrosothiols (hatched bars), were measured at 15, 30, and 60 minutes following L-NMMA infusion, and plotted relative to their measured values at t=0.

Interestingly, when the percentage changes in total S-nitrosothiols, S-nitroso-proteins, and low-molecular-weight S-nitrosothiols were compared in these experiments, a transient increase in low-molecular-weight S-nitrosothiols occurred at 15 minutes, as shown in FIG. 3. These data suggest that transfer of nitric oxide (probably as nitrosonium ion) occurs from S-nitroso-proteins to low-molecular-weight thiols during the course of the re-equilibration of nitric oxide among thiol pools as EDRF production decreases.

Importantly, in vitro experiments suggest that low-molecular-weight thiols can facilitate release of nitric oxide from S-nitroso-proteins, thereby enhancing the vasodilator or platelet inhibitory activity of the protein-bound nitric oxide. For example, glutathione added to a solution containing a molar excess of S-nitroso-bovine serum albumin in phosphate-buffered saline at pH 7.4 led to the rapid formation of stoichiometric concentrations of S-nitroso-glutathione, measured as acid-or acetone-soluble S-nitrosothiol by the photolysis-chemiluminescence method.

The results showed that normal human plasma contains approximately 7 µM S-nitrosothiols, of which 96% are S-nitroso-proteins; 82% of which consists of S-nitroso-serum albumin. In contrast, circulating levels of free nitric oxide are only in the 3 nM range. In rabbits, plasma S-nitrosothiols are present at approximately 1 µM; sixty minutes after administration of 50 mg/ml LNMMA. S-nitrosothiols decreased by approximately 40% (>95% of which were accounted for by S-nitroso-proteins and approximately 80% of which was S-nitroso-serum albumin), and this was accompanied by a concomitant increase in mean arterial blood pressure of 22%.

The inventors have, in addition, demonstrated the formation of approximately 1 μM S-nitroso-protein in human macrophage cell lines (U937 cells) stimulated with 1 mg/ml LPS. This important demonstration provides an explanation for the failure of others in the art to detect nitric oxide in human macrophage cell lines: as in plasma, nitric oxide exists in a biologically active form in cells, as a nitrosonium equivalent bound to thiol.

These data suggest that naturally produced nitric oxide circulates in plasma primarily complexed in S-nitrosothiol species, principal among which is S-nitroso-serum albumin. This abundant, relatively long-lived adduct most likely serves as a reservoir with which plasma levels of highly reactive, short-lived free nitric oxide can be regulated for the maintenance of vascular tone.

DISCUSSION

Currently available analytical methods do not enable the detection of free nitric oxide in biological fluids, nor allow discrimination among nitric oxide, nitrosonium equivalents and important bioactive nitric oxide adducts. This limitation of current methodology has been justified by the general consensus that nitric oxide is metabolized to inactive higher oxides of nitrogen and does not exist in other biologically relevant forms.

These investigators have recently determined (as shown within) that nitric oxide exists in biological systems predominantly as an S-nitroso adduct of proteins in which the nitric oxide moiety behaves chemically as nitrosonium. These adducts are biologically active and possess unique pharmacological properties. In view of the serious and important limitations of the currently methodology, the inventors have developed a new method that enables the detection of nitric oxide in biological fluids, and also enables one to distinguish nitric oxide adducts, such as S-nitroso-proteins and S-nitrosothiols, from free nitric oxide.

Results obtained using this method demonstrate the following: (1) nitric oxide and its related biologically-active adducts can be measured simply, with minimal sample preparation, in a biological fluid; (2) S-nitrosothiols circulate in plasma, and form in cells, primarily as S-nitroso-proteins, the predominant species of which, in plasma, is S-nitroso-serum albumin; (3) pharmacologic interventions that modulate nitric oxide generation change plasma levels of S-nitrosothiols; and (4) nitric oxide equivalents in the form of nitrosonium are present in biological systems.

The abundance of S-nitrosothiols in plasma compared, with that of free nitric oxide which is three to four orders of magnitude lower in concentration, suggests that plasma S-nitrosothiols serve as a reservoir for nitric oxide, effectively buffering its concentration. Protein thiol adducts of nitric oxide are particularly well suited for this role because of their relatively long-half lives under physiologic conditions (Stamler, J. S. et al. *Proc. Natl. Acad. Sci.* 89:444–448 (1992)), as compared with free nitric oxide. Release of nitric oxide or nitrosonium from S-nitroso-protein stores may be brought about by mixed disulfide formation with low-molecular-weight thiols, or facilitated by its transfer from protein thiols to the low-molecular-weight thiols. For example, glutathione is particularly effective in this mechanism under physiologic conditions.

As demonstrated above, biological nitric oxide adducts, such as S-nitrosothiols and S-nitroso-proteins, represent a bioactive nitric oxide pool that has a direct role in the maintenance of physiologic systems. Thus, the significant role of these adducts in various normal physiologic states (such as exercise or food intake), or in various pathophysiologic states (such as septic shock, atherosclerosis, or hypertension) necessitates the need for a method which enables the clinician to monitor the level of true nitric oxide bioactivity in the vascular milieu, and other organ systems. The above-described methods of the invention, provide an effective means for accomplishing this goal.

TABLE 1

MEAN PLASMA LEVELS OF NITRIC OXIDE AND S-NITROSOTHIOLS IN HUMANS

| Free Nitric Oxide | $0.0034 \pm 0.00058$ μM |
| S-nitrosothiols | $7.19 \pm 5.73$ μM |
| S-nitroso-proteins | $6.92 \pm 5.45$ μM |

Values represent the mean ± standard deviation of five different donors. Intra-assay variability was ± 3.0%.

TABLE II

CHANGES IN MEAN BLOOD PRESSURE AND PLASMA S-NITROSOTHIOLS IN RABBITS FOLLOWING ADMINISTRATION OF L-NMMA

|  | Pretreatment | 15 Minutes | 60 Minutes |
| --- | --- | --- | --- |
| Mean Blood Pressure (mm HG) | $65 \pm 5$ | $74 \pm 6$* | $78 \pm 11$* |
| S-Nitrosothiols (μM) | $1.29 \pm 0.57$ | $1.11 \pm 0.51$ | $0.78 \pm 0.26$* |
| S-Nitroso-proteins (μM) | $1.22 \pm 0.55$ | $1.03 \pm 0.44$* | $0.73 \pm 0.23$* |

*$P \leq 0.05$ by two-way analysis of variance and Newman-Keuls comparison to the pretreatment value.

What is claimed is:

1. A method for detecting the amount of S-nitrosothiols in a biological fluid sample, said detection comprising the steps of:

(a) subjecting said sample to photolysis;

(b) quantitating the amount of nitric oxide in said sample by measuring the chemiluminescence signal generated by the chemical reaction between nitric oxide and ozone;

(c) inactivating the chemiluminescence signal-generating capability of any nitric oxide which is associated with a thiol, in a separate sample of said biological fluid;

(d) detecting the nitric oxide in the sample obtained in step (c), using steps (a) and (b); and (e) determining the quantitative difference between the amount of nitric oxide detected in steps (b) and (d) to determine the amount of S-nitrosothiols in said biological fluid sample.

2. The method of claim 1 wherein said chemiluminescence signal-generating capability of nitric oxide which is associated with a thiol is inactivated by treating said sample of step (c) with mercurous ion.

3. A method for detecting the amount of S-nitroso-proteins in a biological fluid sample, said detection comprising the steps of:

(a) subjecting said sample to photolysis;

(b) quantitating the amount of nitric oxide in said sample by measuring the chemiluminescence signal generated by the chemical reaction between nitric oxide and ozone;

(c) inactivating the chemiluminescence signal-generating capability of any nitric oxide which is associated with a protein, in a separate sample of said biological fluid;

(d) detecting the nitric oxide in the sample obtained in step (c) using steps (a) and (b); and (e) determining the quantitative difference between the amount of nitric oxide detected in steps (b) and (d) to determine the amount of S-nitroso-protein in said biological fluid sample.

4. The method of claim 3 wherein said chemiluminescence signal-generating capability of nitric oxide which is associated with a protein is removed by treating said sample of step (c) with a protein-precipitating agent.

5. The method of claim 4, wherein said protein-precipitating agent is selected from the group consisting of trichloroacetic acid, acetone, phenol and ammonium sulfate.

6. The method of claims 1 or 3 wherein said biological sample is a human sample.

7. The method of any one of claims 1 or 3 wherein said biological fluid sample is selected from the group consisting of blood, serum, urine, cerebrospinal fluid, semen, synovial fluid, peritoneal fluid, sputum, intestinal secretions, corneal fluid, amniotic fluid, stool, saliva, and perspiration.

* * * * *